United States Patent
Aggerholm et al.

(10) Patent No.: US 10,456,561 B2
(45) Date of Patent: Oct. 29, 2019

(54) NON-COMPLIANT HIGH STRENGTH MEDICAL BALLOON

(71) Applicant: Cook Medical Technologies LLC, Bloomington, IN (US)

(72) Inventors: Steen Aggerholm, St. Heddinge (DK); Thomas Lysgaard, Solroed Strand (DK)

(73) Assignee: Cook Medical Technologies LLC, Bloomington, IN (US)

( * ) Notice: Subject to any disclaimer, the term of this patent is extended or adjusted under 35 U.S.C. 154(b) by 158 days.

(21) Appl. No.: 14/681,550

(22) Filed: Apr. 8, 2015

(65) Prior Publication Data
US 2015/0297871 A1    Oct. 22, 2015

(30) Foreign Application Priority Data
Apr. 16, 2014  (GB) .................................. 1406850.6

(51) Int. Cl.
*A61M 25/10*    (2013.01)
*D03D 1/00*    (2006.01)
(Continued)

(52) U.S. Cl.
CPC ........ *A61M 25/10* (2013.01); *A61M 25/1029* (2013.01); *D03D 1/00* (2013.01);
(Continued)

(58) Field of Classification Search
CPC .............. A61M 25/10; A61M 25/1029; A61M 2025/1084; D04C 1/06; D03D 3/02;
(Continued)

(56) References Cited

U.S. PATENT DOCUMENTS

| 4,906,244 A | 3/1990 | Pinchuk et al. |
| 5,201,706 A | 4/1993 | Noguchi et al. |

(Continued)

FOREIGN PATENT DOCUMENTS

| WO | WO 96/12516 | 5/1996 |
| WO | WO 97/32624 | 9/1997 |

(Continued)

OTHER PUBLICATIONS

Search and Examination Reports for corresponding priority application GB 1406850.6, dated Nov. 3, 2014, 2p.

(Continued)

*Primary Examiner* — Bhisma Mehta
*Assistant Examiner* — Hamza A Darb
(74) *Attorney, Agent, or Firm* — Brinks Gilson & Lione

(57) ABSTRACT

A non-compliant high strength balloon (10) includes a reinforcement member (30) formed of a sleeve of woven or braided strengthening elements (32, 34). There are provided circumferential strengthening elements (32) which are pre-tensed in order to remove any undulations within the strengthening elements (32) and to ensure that these have a precise annular size. On the other hand, the longitudinal strengthening elements (34) have undulations therein. The pre-tensing of the strengthening elements (32) ensures that the balloon will not stretch during pressurization thereof, which can occur when the circumferential strengthening elements have undulations therein, which will be natural artefacts of a weaving or braiding process. The undulations in the longitudinal strengthening elements (34) provides the balloon with increased longitudinal flexibility.

14 Claims, 4 Drawing Sheets

(51) Int. Cl.
*D03D 3/02* (2006.01)
*D03D 15/02* (2006.01)
*D04C 1/06* (2006.01)

(52) U.S. Cl.
CPC .............. *D03D 3/02* (2013.01); *D03D 15/02* (2013.01); *D04C 1/06* (2013.01); *A61M 2025/1084* (2013.01); *D10B 2201/02* (2013.01); *D10B 2321/0211* (2013.01); *D10B 2331/04* (2013.01); *D10B 2331/10* (2013.01); *D10B 2509/06* (2013.01)

(58) Field of Classification Search
CPC ...... D03D 1/00; D03D 15/02; D10B 2201/02; D10B 2321/0211; D10B 2331/04; D10B 2331/10; D10B 2509/06
See application file for complete search history.

(56) References Cited

U.S. PATENT DOCUMENTS

| | | | |
|---|---|---|---|
| 5,755,690 | A | 5/1998 | Saab |
| 6,156,254 | A | 12/2000 | Andrews et al. |
| 6,746,425 | B1 | 6/2004 | Beckham |
| 8,313,601 | B2 | 11/2012 | Pepper et al. |
| 2002/0161388 | A1* | 10/2002 | Samuels ............... A61L 29/085 606/192 |
| 2004/0002729 | A1 | 1/2004 | Zamore |
| 2004/0082965 | A1 | 4/2004 | Beckham |
| 2004/0109964 | A1 | 6/2004 | Beckham |
| 2005/0123702 | A1 | 6/2005 | Beckham |
| 2006/0008606 | A1 | 1/2006 | Horn et al. |
| 2006/0085022 | A1 | 4/2006 | Hayes et al. |
| 2007/0059466 | A1 | 3/2007 | Beckham |
| 2007/0093865 | A1 | 4/2007 | Beckham |
| 2007/0250101 | A1 | 10/2007 | Horn et al. |
| 2007/0265565 | A1 | 11/2007 | Johnson |
| 2008/0033477 | A1 | 2/2008 | Campbell et al. |
| 2008/0183132 | A1 | 7/2008 | Davies et al. |
| 2009/0099517 | A1 | 4/2009 | Steadham |
| 2009/0299327 | A1 | 12/2009 | Tilson et al. |
| 2010/0243135 | A1 | 9/2010 | Pepper et al. |
| 2010/0318029 | A1* | 12/2010 | Pepper ................. A61M 25/10 604/103.07 |
| 2011/0046654 | A1 | 2/2011 | Kupperathanam |
| 2011/0120629 | A1 | 5/2011 | Beckham |
| 2012/0101435 | A1 | 4/2012 | Beckham |
| 2012/0277672 | A1 | 11/2012 | Pepper et al. |
| 2012/0277783 | A1 | 11/2012 | Cummins et al. |
| 2012/0296363 | A1 | 11/2012 | Davies, Jr. et al. |
| 2013/0087264 | A1 | 4/2013 | Beckham |
| 2013/0255866 | A1 | 10/2013 | Beckham |

FOREIGN PATENT DOCUMENTS

| | | |
|---|---|---|
| WO | WO 02/068011 A1 | 9/2002 |
| WO | WO 03/074115 A1 | 9/2003 |
| WO | WO 2006/034396 A2 | 3/2006 |
| WO | WO 2006/086516 A3 | 8/2006 |
| WO | WO 2012/009486 A2 | 1/2012 |

OTHER PUBLICATIONS

Raja, Yogesh et. al., "A Noncompliant, High Pressure Balloon to Manage Undilatable Coronary Lesions," *Wiley Interscience*, 2009, 5p, UK.

European Search Report for corresponding European application EP 15275051.9, dated Sep. 9, 2015, 5p.

Office Action for corresponding European application EP 15 275 051.9, dated Dec. 7, 2017, 3p.

* cited by examiner

NON-COMPLIANT HIGH STRENGTH MEDICAL BALLOON

CROSS REFERENCE TO RELATED APPLICATION

This application claims priority to GB application no. 1406850.6, filed Apr. 16, 2014, titled "Non-Compliant High Strength Medical Balloon," the contents of which are incorporated herein by reference.

TECHNICAL FIELD

The present invention relates to a medical balloon and in particular to a high strength medical balloon having non-compliant properties.

BACKGROUND ART

Medical balloons are well known in the medical field and are used, for example, in the deployment of implantable medical devices such as stents and stent grafts, for angioplasty procedures, for temporary vessel occlusion, in valve repair procedures and so on. Often, it is desirous to inflate the balloon to a high pressure, particularly to dilate or otherwise open a vessel, to deploy a medical device and so on. However, a standard medical balloon formed only of a layer of polymer material is liable to rupture, leading to an abortive procedure and possible loss of balloon wall material into the patient's vasculature. Balloon rupture can also occur in cases where the balloon is scraped across a sharp object, such as plaque or other stenosis material within the vessel, or on a part of the medical device deployed off of the balloon.

It is also advantageous in many instances to have a balloon of reliable inflated diameter, that is of a diameter which will not vary over a range of balloon operating pressures. However, the materials commonly used for medical balloons do generally exhibit some stretch as inflation pressure increases, leading to the balloon having a non-constant inflated diameter over a range of operating pressures.

Problems can also occur during angioplasty procedure, when the clinician increases the pressure in the balloon in order to try to break the stenosis. When the stenosis does eventually break, this can lead to rapid expansion of the balloon and risk of it expanding beyond the natural diameter of the vessel.

The risk of balloon rupture can be reduced or avoided by the use of a strengthening sleeve disposed around the balloon, which may usefully be made of woven or braided fibers. Strengthening sleeves of this type are generally considered to retain flexibility of the balloon particularly when this is folded and wrapped. Such flexibility is a characteristic which is important in maintaining trackability during endoluminal insertion of the medical balloon into a patient.

A problem occurs with such strengthening sleeves is that as a result of the braiding or weaving of the sleeve, there is still experienced some expansion of the strengthening sleeve during inflation of the balloon, which causes the balloon to exhibit some variation in its inflated diameter.

Some examples of prior art medical balloons are disclosed in US 2012/0277783, US 2011/0046654, US 2006/0085022, U.S. Pat. Nos. 5,201,706 and 6,156,254.

DISCLOSURE OF THE INVENTION

The present invention seeks to provide an improved medical balloon and in the preferred embodiments a medical balloon exhibiting generally no compliance with changes in inflation pressures within an operating pressure range. The present invention also seeks to provide an improved method of making such a balloon.

According to an aspect of the present invention, there is provided a method of making a reinforced medical balloon, the balloon formed from a balloon structure and including a balloon body member having a circumferential dimension, a longitudinal dimension, and an annular shape in the circumferential dimension; including the steps of: fitting a reinforcement member to the balloon structure, the reinforcement member being formed of an array of reinforcement elements interleaved with one another so as to include circumferential elements and longitudinal elements, the reinforcement member being fitted such that the circumferential elements extend in the circumferential dimension of the balloon and substantially transversally to the longitudinal dimension; wherein the fitting step includes the step of tensing the circumferential elements so as to cause the circumferential elements to adopt a circular annular shape in the circumferential dimension.

This method provides strengthening elements which are arranged circumferentially and which are pre-tensed, which causes them to adopt an annular shape ensuring that the circumferential elements have no undulations or other curves or bends which would enable them to stretch, or straighten, as the balloon is inflated. In other words, the characteristic of a circular annular shape is one which has no undulations remaining form the weaving, braiding or knitting process. The balloon therefore has a reliable and consistent inflated diameter. When the circumferential elements are formed of non-compliant material, the balloon will have a single and non-varying diameter across the range of operating pressures applied to the balloon. Preferably, the circumferential strengthening elements are disposed precisely circumferentially without any component in the longitudinal direction.

Advantageously, the longitudinal elements are not tensed during the step of tensing the circumferential elements. In cases where the strengthening elements are woven or braided together, tensing the longitudinal elements as well as the circumferential elements will not allow the circumferential elements to adopt a truly annular form, leading still to variations in their diameter as the balloon is inflated. Furthermore, leaving the longitudinal elements untensed will cause them in this example to be somewhat looser in form relative to the circumferential elements, thereby increasing the flexibility of the balloon in the longitudinal direction, seen as advantageous in assisting the balloon to take a curved longitudinal shape and in increasing the flexibility of the balloon during the introduction and deployment processes. In this regard, the longitudinal elements may have an undulating form.

In an embodiment, tensing of the circumferential elements causes or increases undulations in the longitudinal elements.

At least the circumferential elements are embedded in or substantially completely attached to the balloon body member. This arrangement ensures good coupling of the reinforcement member to the balloon and as a result precise conformity of the performance of the balloon with that of the reinforcement member. It is not, though, necessary for the reinforcement member to be embedded into the balloon wall.

Advantageously, the circumferential strengthening elements are formed from non-compliant material. The longitudinal strengthening elements may likewise be formed of non-compliant material but could equally be formed of compliant material, thereby enhancing longitudinal flexibility of the balloon. Non compliant materials include any materials which will exhibit negligible stretch at the stresses created during normal operating pressures of the balloon.

The reinforcement member is advantageously a woven structure, although could also be braided. Preferably, the reinforcement member is formed of threads or wire. In a practical embodiment, the reinforcement element is a two dimensional woven structure. It will be appreciated that the warp and weft of a woven structure and the direction of braiding of a braided structure will advantageously extend in the circumferential dimension of the balloon and preferably (although not necessarily) in the longitudinal dimension.

According to another aspect of the present invention, there is provided a reinforced medical balloon, including: a balloon body member, the balloon body member having a circumferential dimension, a longitudinal dimension and an annular shape in the circumferential dimension; a reinforcement member formed of an array of reinforcement elements interleaved with one another so as to include circumferential elements and longitudinal elements, the circumferential elements extending in the circumferential dimension of the balloon and substantially transversally to the longitudinal dimension; wherein the circumferential elements are tensed during manufacture of the medical balloon to adopt a circular annular shape in the circumferential dimension. Specifically, the circumferential elements have a circular annular shape in the circumferential dimension when the balloon is inflated to a minimum inflation pressure, which is before the balloon is stretched by inflation pressure. This is achieved by tensing the circumferential elements during manufacture of the medical balloon to adopt the circular annular shape.

In summary, therefore, the preferred embodiment provides a non-compliant high strength balloon which includes a reinforcement member formed of a sleeve of woven or braided strengthening elements. There are provided circumferential strengthening elements which are tensed during manufacture of the balloon in order to remove any undulations within the strengthening elements and to ensure that these have a precise annular size. On the other hand, the longitudinal strengthening elements have undulations therein. Such pre-tensing or straightening of the strengthening elements ensures that the balloon will not stretch during pressurization thereof, which can occur when the circumferential strengthening elements have undulations, which will be natural artefacts of a weaving or braiding process. The undulations in the longitudinal strengthening elements provide the balloon with increased longitudinal flexibility.

The balloon can have any of the features disclosed above and elsewhere herein.

BRIEF DESCRIPTION OF THE DRAWINGS

Embodiments of the present invention are described below, by way of example only, with reference to the accompanying drawings, in which.

DESCRIPTION OF THE PREFERRED EMBODIMENTS

Figure 1:
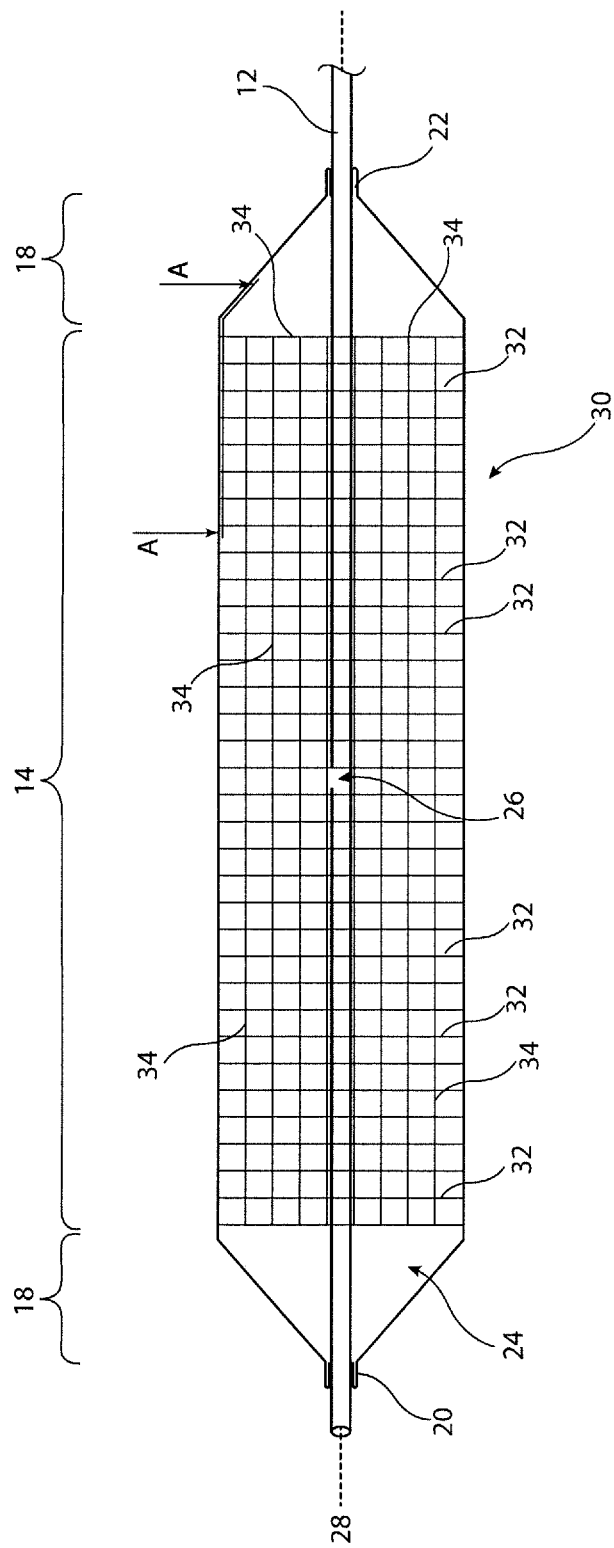
FIG. 1 is a schematic diagram of a side elevational view of an embodiment of non-compliant high strength medical balloon.

The accompanying drawings are schematic only. It is to be understood that the dimensions and proportions of the various components of the devices shown in the drawings are not to scale or in proportion relative to one another. It is also to be understood that the drawings depict only the principal components of the device shown therein and that other elements and components of the device which are not central to understanding the teachings herein have been omitted for the sake of clarity.

The embodiments depicted in the drawings show a medical balloon having a body portion which is substantially cylindrical. It is to be appreciated, though, that the shape of the medical balloon does not need to be as depicted in the drawings and in particular does not need to have a cylindrical body portion. Other embodiments may have a balloon body portion which, for example, is tapered so as to have a larger diameter at one end relative to the other, has a waist at a central region thereof, or any other shape. It is preferred, though, that the balloon body portion is annular in transverse cross-section throughout its length, for reasons which will become apparent below.

The teachings herein are applicable to any medical balloon including, for example, delivery of balloons used for delivering implantable medical devices, angioplasty balloons, valve treatment balloons and so on.

Referring first to FIG. 1, this shows an embodiment of medical balloon 10 which is fitted to a balloon catheter 12, which may be of any known form. The balloon includes a body portion 14 which in this embodiment is substantially cylindrical along its length and is annular in transverse cross-section. At either end of the body portion 14, the balloon includes end cones 16, 18 which taper towards necks 20 and 22 of the balloon 12. The necks 20, 22 are fixed to the balloon catheter 12 in fluid tight manner, typically by fusing or bonding with an adhesive or other bonding agent. Suitable methods for fixing the balloon 10 to balloon catheter 12 are well known in the art.

The balloon has an internal chamber 24 which surrounds the portion of the balloon catheter 12 between the necks 20 and 22. The chamber 24 can be filled or emptied, typically with saline solution, via a port 26 in the balloon catheter 12 which communicates with a lumen within the catheter 12, as is known in the art.

The balloon 10 is generally made of a consistent balloon wall material along its entire length, that is its body portion 14, the end cones 16, 18 and the necks 20, 22. Typically, the balloon 10 is formed of a thin and strong material, for example polyamide such as Nylon, polyether block amide such as Pebax, polyethylene terephthalate (PET), polyethylene, polyurethane, among others. It is to be understood that these are only examples of suitable for balloon materials and the skilled person will be readily able to identify other suitable materials. The material of the medical balloon may be compliant, that is of a nature which will stretch upon the application of stress or inflation pressure to the balloon 10, and may also be of a substantially non-compliant material, that is one which is less liable to stretch upon inflation of the balloon 10. It is generally desired to make the wall of the balloon 10 as thin as possible as this increases the wrappability and foldability of the balloon 10 for deployment purposes and in particular in order to reduce the footprint of the balloon catheter for endoluminal delivery through the patient's vasculature and also to be able to treat very small diameter vessels including, for example, the cerebral vessels.

The balloon 10 could be formed of a single layer of material but in other embodiments could be made of a plurality of layers of material, each having different characteristics. In one example, the balloon 10 may have an outer layer of material which has a lower softening or melting temperature compared to the material used for one or more inner layers of the balloon. This allows the outer layer of the balloon to soften or melt during the manufacture of the balloon 10, for purposes which will be described below.

Indicated generally at 30 is a reinforcement member which in this embodiment is in the form of a cylindrical sleeve extending across the entirety of the body portion 14 of the balloon. In some embodiments the reinforcement member 30 may also extend also along the end cones 16 and 18 and at least partially along the length of the necks 20 and 22. A reinforcement member which extends along substantially the entire length of the balloon 10 will provide reinforcement over the entire length of the balloon 10, although for reasons which will become apparent below, the end cones 16, 18 tend to have thicker walls than the balloon body portion 14 and thus generally require less strengthening. The reinforcement member 30 has a shape equivalent of that of the balloon body portion 14 and therefore will not necessarily be cylindrical. The sleeve 30 is, though, annular in transverse cross-section.

The reinforcement member 30 includes circumferential strengthening elements 32 which extend circumferentially around the balloon body portion 14. The circumferential strengthening elements 32 are preferably of sufficient density, that is spacing from one another, to provide reinforcement to the balloon 10 and in particular the body portion 14 when the balloon 10 is inflated to operating pressures. Typical densities of the circumferential strengthening elements 32 may be, for example: dtex 55 (denier 50). Typical densities of the longitudinal strengthening elements 34 may be, for example, dtex 25 (denier 23).

The circumferential reinforcing elements 32 may have a thread diameter of around 17 micrometers, while the longitudinal fibers may have a diameter of around 12 micrometers. An example of E-modulus is cN/dtex of 1100 for the circumferential elements 32 and cN/dtex of 1250 for the longitudinal elements 34. Thread or wire diameter can vary with different balloon sizes, as can fiber densities. The skilled person will also recognize that these parameters are exemplary only and that other fiber sizes and densities can be used and will be within the ability of the skilled person to determine readily.

The circumferential strengthening elements 32 preferably extend precisely orthogonal to the longitudinal axis 28 of the balloon 10, that is precisely in the circumferential direction or dimension of the body portion 14.

The reinforcement member 30 also includes an array of longitudinally disposed strengthening elements 34 which in this example are parallel to the longitudinal axis 28 of the balloon 10. It is, though, not essential that the longitudinally disposed strengthening elements 34 are precisely aligned to the longitudinally axis of the balloon 10. They could, for example, be at an angle to this, anything from a few degrees to much greater angles including, for instance, up to 45° or more.

The strengthening elements 32 and 34 may have a variety of forms including, for example, flat strips of material. It is preferred, though, that the strengthening elements are made of threads or wires, which enables them to be woven or braided together to form what could be described as a unitary sleeve. The circumferential strengthening elements 32 are best made of a non conformable material, that is a material which will not elongate over the range of operating pressures to which the balloon 10 is intended to be used. Suitable materials for the circumferential strengthening elements include: ultrahigh molecular weight polyethylene such as Dyneema™, polyester, cotton or other suture material. The circumferential strengthening elements could also be made of a metal or metallic wire.

The longitudinal strengthening elements 34 may be made of the same material as the circumferential strengthening elements 32 but may also be made of other materials, including compliant materials such as: polyurethane and spandex.

Each of the strengthening elements 32, 34, when formed of a thread or wire, could be of a single filament or of multi-filament form. When made of a multi filament form, it is preferred that the filaments are intertwined such that each strengthening element 32 is a unitary structure with consistent characteristics.

In some embodiments the strengthening elements 32 and/or 34 could have radiopaque characteristics, such as including some radiopaque components, for instance metallic threads or the like.

Figure 2:
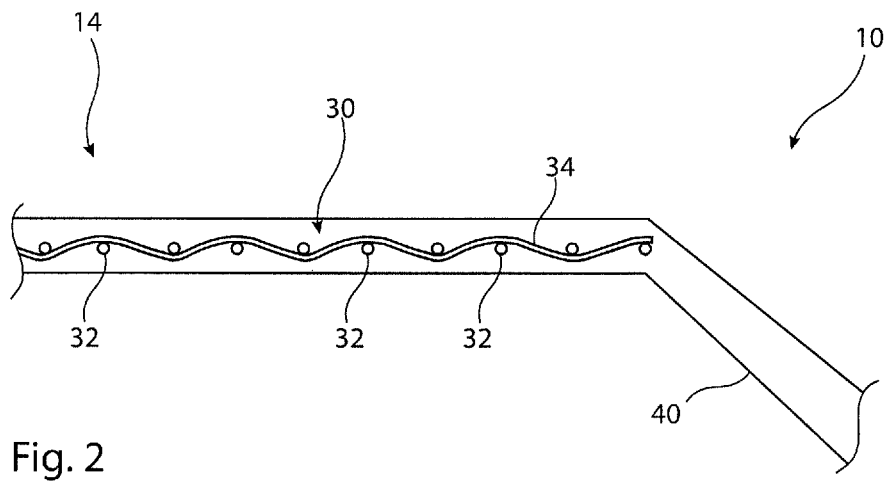
FIG. 2 is a cross-sectional view of a part along line A-A of the balloon of FIG. 1.
Figure 3:
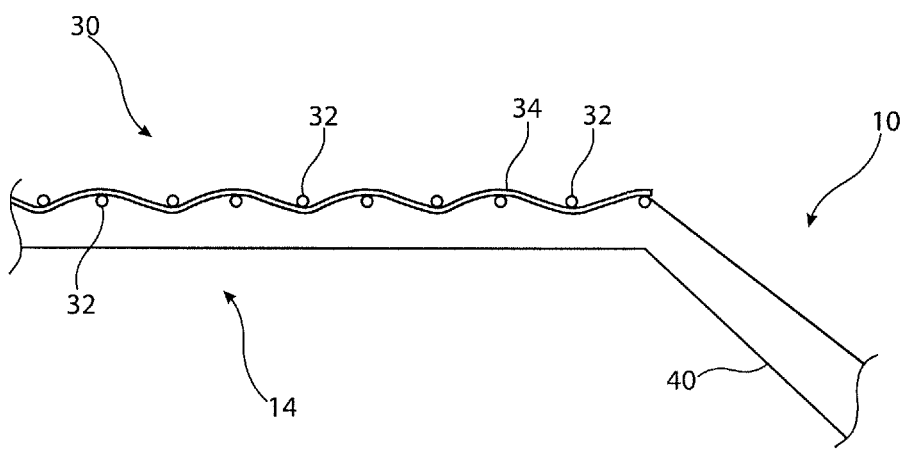
FIG. 3 is a cross-sectional view of a part of another embodiment of high strength balloon along line A-A of FIG. 1.

Referring now to FIGS. 2 and 3, these show two examples as to how the reinforcement member 30 may be applied to the balloon 10. Each of FIGS. 2 and 3 discloses a portion of the medical balloon 10 between lines A-A of FIG. 1. The characteristics shown in FIGS. 2 and 3, though, appear over the whole extent of the strengthening member 30.

With reference to FIG. 2 first, this depicts a medical balloon 10 having a balloon wall 40 formed of a single layer of any of the materials described above. The reinforcement member 30 is in this example wholly embedded within the thickness of the balloon wall 40, such that no part of the reinforcement member 30 extends beyond the surfaces of the balloon wall 40. The circumferentially extending strengthening elements 32 are shown in cross-section in FIG. 2 and extend in and out of the view of FIG. 2. The longitudinally extending strengthening elements 34, as can be seen in FIG. 2, undulate along the length of the body portion 14 of the balloon 10 and in this example in and out of the circumferential strengthening elements 32, that is extend over one element 32 underneath the adjacent circumferential element, over the next, under the one after and so on. Such an arrangement can typically be achieved by weaving or braiding.

FIG. 3 shows a slightly different arrangement, in which the reinforcement member is only partially embedded within the balloon wall 40, such that the reinforcement member 30 extends to the outer surface of the medical balloon 10. This can have the effect of texturing or roughening the outer surface of the balloon 10, useful in holding a medical device on the balloon 10, or in maintaining the position of the balloon 10 reliably within a patient's vessel or across a valve opening. The arrangement of FIG. 3 can be achieved by only partially softening or melting the wall 40 of the balloon 10 during the balloon formation process and equally can be achieved by forming the balloon wall 40 of a plurality of different layers of which an outermost, relatively thin, layer is formed of a material having a lower melting or softening temperature than the internal layer or layers of the balloon wall 40, such that during formation of the balloon only the outer layer will melt sufficiently to bond to the reinforcement member 30, as will be described in further detail below.

As with the example of FIG. 2, the longitudinally disposed strengthening element 34 shown in FIG. 3 undulates in and out of the circumferentially arranged strengthening elements 32, which can be seen in cross-section in FIG. 3.

In other embodiments, the reinforcement member 30 may be bonded to the balloon 10, for example by means of a suitable adhesive or other bonding agent.

Figure 4:
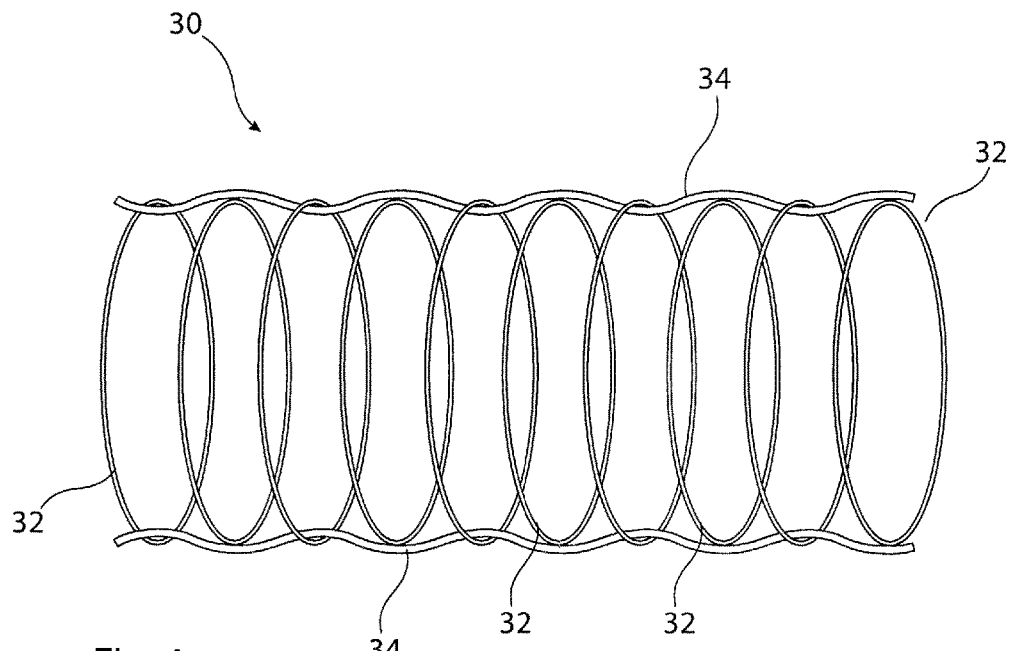
FIG. 4 is a schematic diagram depicting the strengthening member of the balloon of FIGS. 1 to 3.

Referring now to FIG. 4, this shows in schematic form a perspective view of the structure of the reinforcement member shown in FIGS. 1-3. The circumferential or annular strengthening elements 32 are shown by the oval shapes in FIG. 4 whereas just a few longitudinally disposed strengthening elements 34 are shown in the drawing. The skilled person will appreciate that in practice the reinforcement member would be formed of a much larger number of circumferential and longitudinal strengthening elements 32, 34 in a relatively tight weave or braid. Examples will include a weave or braid of around 20 denier to around 50 denier. The circumferential strengthening elements 32 preferably have a precise annular shape, that is are circular. On the other hand, the longitudinally oriented strengthening elements 34 undulate along the length of the reinforcement member 30 and therefore are not straight. In practice, as is described in further detail below, the circumferential strengthening elements 32 are stretched following the formation of the reinforcement member 30 so that the circumferential elements 32 are tensed or straightened to an annular shape. This is achieved by a differential stretching of the reinforcement member 30, that is by stretching it solely or principally in the circumferential (radial) direction. This differential stretching straightens the circumferential elements 32 and removes any undulations therein, in preference to the longitudinally arranged elements 34. Thus, by radially stretching the reinforcement member 30, any undulations within the circumferential elements 32 formed during the weaving or braiding process will be "stretched out", typically also resulting in the formation of greater undulations in the longitudinally arranged strengthening elements 34. The result is that the radial strengthening elements 32 will in practice not expand radially beyond their diameter as depicted in FIG. 4 during inflation of the balloon because any undulations within the circumferential elements 32 will already have been removed. Therefore, the reinforcement member 30 will have a definite and singular diameter when the balloon to which the reinforcement member 30 is applied is inflated.

In practice, the balloon 10 will be folded and wrapped over the balloon catheter 12 for deployment. The reinforcement member 30 will be folded and wrapped just in the same way as the balloon 10 by virtue of being integral with or bonded to the balloon 10. However, the reinforcement member 30 and therefore the balloon 10 will retain the same circumferential size even when wrapped and folded, meaning that as the balloon is inflated, the balloon will do so to the diameter of the circumferential strengthening elements 32 and will not expand beyond that diameter for virtue of the constriction generated by the circumferential strengthening elements 32. This contrasts with prior art strengthening sleeves which are simply braided or woven, where the circumferential strengthening elements or any strengthening elements having a circumferential component thereto have undulations therewithin. Such prior art strengthening sleeves will, as a result, fail to provide a balloon having a truly non-variable inflated diameter as the diameter will change from the undulated to the non-undulated form of the circumferential strengthening elements thereof.

Referring again to FIG. 4, the skilled person will now appreciate that the longitudinally extending strengthening elements 34 have an undulating form and in some embodiments with greater undulations than a simple woven structure which is not differentially stretched. This gives the reinforcement member 30 greater flexibility in the longitudinal direction, which can be particularly advantageous in some medical applications, for instance in giving the balloon 10 greater ability to conform to the shape of a curved lumen. A balloon which has relatively rigid longitudinal strengthening elements will not curve easily to conform to a curved lumen and will therefore apply disadvantageous straightening forces to the vessel.

As explained above, the longitudinal strengthening elements 34 could in some embodiments be formed of a conformable material, that is an elastic material, further enhancing the flexibility of the reinforcement member 30 in the longitudinal direction.

The structure shown in FIG. 4 and which is applicable to all the embodiments disclosed herein, provides a balloon which will unfold and unwrap upon inflation to a given diameter, generally the diameter of the circumferential strengthening elements 32. The balloon can be inflated to a greater pressure without any change in that diameter, or a change which is minimal and having no appreciable effect on the characteristics or performance of the balloon 10. As a result, the balloon 10 can be deployed at a variety of inflation pressures while retaining the same operating diameter. This can be particularly useful, for example, in angioplasty procedures, where it may be necessary to increase the pressure within the balloon 10 in order to open the vessel but where it is important to ensure that the vessel is not dilated beyond the desired diameter. Similar considerations can also apply in the deployment of medical devices carried on the balloon, as well as in valve treatment and so on.

Figure 5:
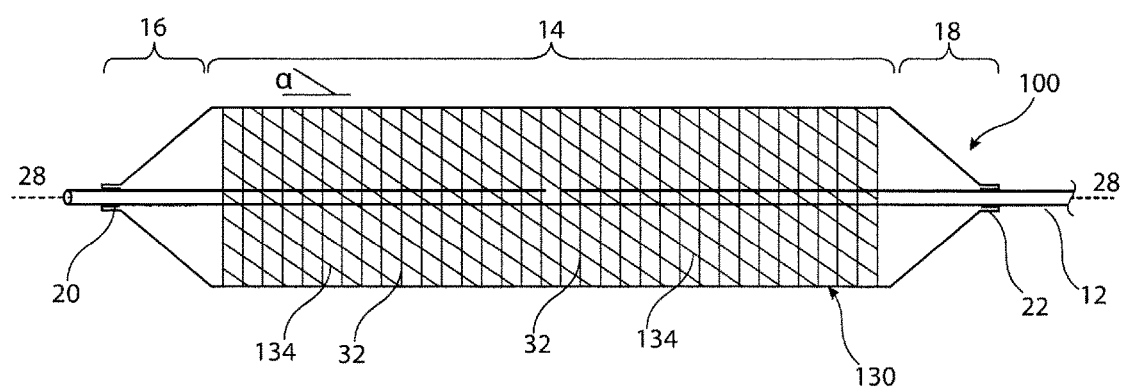
FIG. 5 is a schematic diagram of a side elevational view of another embodiment of non-compliant high strength medical balloon.

Referring now to FIG. 5, there is shown another embodiment of medical balloon 100 very similar to the medical balloon 10 shown in FIGS. 1 to 3. The medical balloon 100 has a balloon body portion 14 bounded by first and second end cones 16, 18 which extend to necks 20, 22 attached to a balloon catheter 12, just as in the embodiment of FIG. 1. A reinforcement member 130 extends over the body portion 14 and is in the form of a sleeve having a shape consistent with that of the body portion 14, in this example being cylindrical and annular in axial cross-section. The reinforcement member 130 includes circumferential strengthening elements 32, the same as the strengthening elements 32 of the embodiment of FIG. 1, as well as longitudinal strengthening elements 134 having a similar structure and made from similar materials to the longitudinal strengthening elements 34 of the embodiment of FIG. 1. The principal difference with the longitudinal strengthening elements 134 is that they extend helically around the body portion 14, at an angle α to the longitudinal axis 28 of the balloon 100 and which may be anything from a few degrees to 30, 40 or even up to 45° from the axis 28. The longitudinal strengthening elements 134 are useful in providing a cohesive structure to the reinforcement member 30, for instance by allowing for weaving or braiding with the circumferential strengthening elements 132, and also in providing longitudinal strengthening of the balloon without unduly reducing the flexibility of the balloon 100.

The person skilled in the art will appreciate that a variety of forms of longitudinal strengthening elements could be used with a balloon according to the teachings herein.

Figure 6:
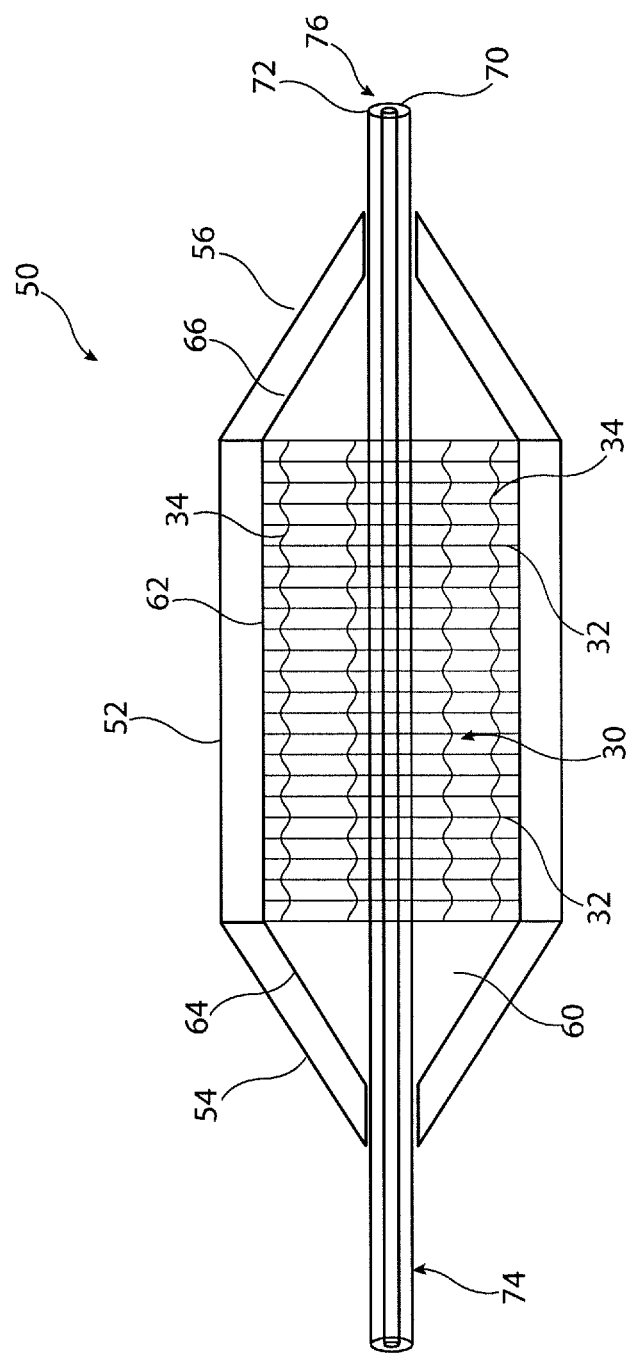
FIG. 6 is a schematic diagram of an example of balloon forming apparatus for the manufacture of a medical balloon as taught herein.

Referring now to FIG. 6, this shows an embodiment of apparatus 50 for the manufacture of a medical balloon as disclosed herein. It is to be appreciated that the apparatus is shown in schematic form only. In this example the apparatus 50 has three mold components 52, 54 and 56, which are shown in cross-section in FIG. 6. The first mold component 52 has a generally circular cylindrical inner surface 62 which in practice conforms to the final shape of the body member 14 of the medical balloon. The end elements 54 and 56 have internal conical surfaces which have a shape conforming to the end cones 16, 18 of the medical balloon. Typically, the components 52-56 are separable components in order to be able to remove the formed balloon from within the mold chamber 60. Molds of such a nature are known in the art.

Raw tubing 70 provides the balloon structure and is made of the material which forms the balloon wall. It may thus be of a single or multiple layers. The raw tubing 70 includes a lumen 72 therein for the passage of inflation fluid. The mold 50 has at its ends suitable restraining devices (not shown) for holding the raw tubing 70 to the mold during the blowing process. Suitable restraining devices are known in the art.

As can be seen in FIG. 6, disposed within the cylindrical section 52 of the mold 50 is a reinforcement member or sleeve 30, which can conveniently already be in an open configuration but may equally be at least partially folded within the mold. The reinforcement member 30 envelops the raw tubing 70, as will be apparent from FIG. 6.

In order to blow a balloon from the raw tubing 70, one end, for example end 74, is closed. Inflation fluid under pressure is then fed into the balloon from the other end 76 via a suitable feed mechanism (not shown but known in the art). The mold 50 is also heated in order to heat the material of the raw tubing 70 which, under inflation pressure, will then soften and begin to expand radially outwardly, eventually up to the surfaces 62, 64 and 66 of the mold 50. In some embodiments, at least the outer layer of the raw tubing 70 is made of a material which will significantly soften or melt during the blowing process, which will cause the balloon material to flow into and around the elements of the reinforcing member 30 in order at least partially to embed the reinforcement member 30 into the wall of the balloon.

In cases where the entirety of the strengthening sleeve 30 is to embedded into the balloon wall, as depicted in FIG. 2, the tensed diameter of the circumferential strengthening elements 32 is chosen to be slightly less than the diameter of the internal surface 62 of the mold section 52. In one example, the reinforcement member 30 may have a woven or braided diameter of around 17 mm for fitting to a balloon of 20 mm diameter. The stretched or tensed diameter of the reinforcement member 30, that is of the circumferential strengthening elements 32, will be greater than 17 mm and slightly less than 20 mm, for instance 19 mm or so. It will be appreciated that the diameter of the circumferential strengthening elements 32, when stretched or tensed to have their undulations removed, is between the diameters of the inner and outer wall surfaces of the balloon wall 40 and to an extent determined by the thickness of the balloon wall. In embodiments where the reinforcement member 30 is to extent radially beyond the balloon wall 40, as in the example of FIG. 3, the circumferential strengthening elements 32 will have a stretched diameter at least as large as the diameter of the outer surface of the balloon wall 40.

As the raw tubing 70 is inflated and heated, the material of the raw tubing, whether only the outer layer in a multi-layer tubing or the entirety of the tubing layer, will soften, enabling the raw tubing to expand when pressurized. The inflating raw tubing will eventually come into abutment with the reinforcement member 30. Further expansion will cause the reinforcement member 30 and in particular the circumferential strengthening elements 32 to tense, smoothing out the undulations in the elements 32 produced during weaving or braiding and thus causing the circumferential elements 32 to attain their maximum diameter.

In accordance with the embodiment of FIG. 2, further heating and inflation of the raw tubing will cause the outermost parts thereof to flow around, into and eventually beyond the diameter of the strengthening elements 32, 34, causing the reinforcement member 30 to become entirely embedded within the volume of the thus formed balloon wall. As there is virtually no elongation of the raw tubing 70 at least within section 52, the longitudinally oriented strengthening elements 34 will not be stretched and therefore will retain an undulating shape. In practice, the undulations in the longitudinal strengthening elements 34 may become more pronounced as a result of the stretching of the circumferential strengthening elements 32. The balloon assembly will therefore take the characteristics shown in Figures during the step of blowing of the balloon.

Once the raw tubing has been inflated to the inner surfaces of the mold 50 to form the balloon, the balloon is allowed to cool and the inflation fluid is then removed, allowing the balloon to be deflated and folded. The reinforcement member 30 and in particular the stretched circumferential strengthening elements 32 will wrap and fold with the balloon but will not reacquire any undulations.

When it is desired to have the reinforcement member 30 bonded to or only partially embedded within the balloon wall, the tensed diameter of the reinforcement member 30, in particular of the circumferential strengthening elements 32, is preferably the same as or about the same as the internal diameter of the internal surface 62 of the mold section 52. Thus, the sleeve 30 will be in contact with and press against the mold surface 62 during the balloon forming process. Similar characteristics would also apply to embodiments in which the reinforcement member 30 is bonded to the balloon, for example by adhesive of other bonding agent.

The medical balloon disclosed herein could have a smooth outer surface but equally could be provided with cutting or scoring elements, particularly useful when the balloon is used as an angioplasty device. Cutting or scoring elements could be integrally formed with the balloon during the balloon blowing process depicted in FIG. 6, in which case the raw tubing and/or inner surface of the mold may have provision for the formation of scoring elements made from balloon wall material, or for attaching or embedding scoring elements to the balloon wall.

The invention claimed is:

1. A method of making a reinforced medical balloon, the balloon formed from a balloon structure and including a balloon body member having a circumferential dimension, a longitudinal dimension, and an annular shape in the circumferential dimension; including the steps of:

fitting a reinforcement member to the balloon structure, the reinforcement member being formed of an array of reinforcement elements interleaved with one another so as to include a plurality of circumferential elements and a plurality of longitudinal elements, the plurality of longitudinal elements being disposed substantially parallel to the longitudinal dimension and alternatively extending over and then under adjacent ones of the plurality of circumferential elements so as to form the reinforcement member with woven or braided elements, the reinforcement member being fitted such that the plurality of circumferential elements extend in the circumferential dimension of the balloon and are disposed substantially transversally to the longitudinal dimension;

wherein the fitting step includes a step of solely tensing the plurality of circumferential elements following formation of the reinforcement member so as to cause both the plurality of circumferential elements to adopt a circular annular shape in the circumferential dimension and the plurality of longitudinal elements to adopt an undulating shape, and wherein the step of tensing the plurality of circumferential elements is performed without inflating the balloon body member.

2. A method according to claim 1, wherein the plurality of longitudinal elements are not tensed during the step of tensing the plurality of circumferential elements.

3. A method according to claim 1, wherein the step of tensing of the plurality of circumferential elements causes or increases undulations in the plurality of longitudinal elements, and wherein the undulations of each of the plurality of longitudinal elements are disposed within.

4. A method according to claim 1, wherein at least the plurality of circumferential elements are at least partially embedded in or attached to the balloon body member.

5. A method according to claim 1, wherein at least the plurality of circumferential elements are completely embedded in the balloon body member.

6. A method according to claim 1, wherein the plurality of circumferential elements are formed from non-compliant material.

7. A method according to claim 1, wherein the reinforcement member is a woven structure.

8. A method according to claim 7, wherein the reinforcement member is a two dimensional woven structure.

9. A method according to claim 1, wherein the reinforcement member is a braided structure.

10. A method according to claim 1, wherein the fitting step is performed prior to inflating the balloon body member.

11. A method according to claim 1, wherein undulations of each of the plurality of longitudinal elements are disposed within a plane that is perpendicular to a radial longitudinal cross-section of a wall of the balloon body member, the radial longitudinal cross-section being parallel to the longitudinal dimension.

12. A reinforced medical balloon, comprising:
a balloon body member, the balloon body member having a circumferential dimension, a longitudinal dimension, and an annular shape in the circumferential dimension;
a reinforcement member formed of an array of reinforcement elements interleaved with one another so as to include a plurality of individual spaced apart circumferential elements and a plurality of longitudinal elements, the plurality of longitudinal elements being disposed substantially parallel to the longitudinal dimension and alternatively extending over and then under adjacent ones of the plurality of circumferential elements so as to form the reinforcement member with woven or braided elements, the plurality of circumferential elements extending in the circumferential dimension of the balloon and being disposed substantially perpendicular to the longitudinal dimension;
wherein the plurality of circumferential elements are tensed during manufacturing of the medical balloon and following formation of the reinforcement member to adopt both a circular annular shape in the circumferential dimension and an undulating shape in the longitudinal dimension when the balloon body member is in an uninflated state, and
wherein the circular annular shape in the circumferential dimension and the undulating shape in the longitudinal dimension is maintained when the balloon body member is in an inflated state.

13. A balloon according to claim 12, wherein the plurality of longitudinal elements have an undulating form.

14. A balloon according to claim 12, wherein the plurality of circumferential elements are formed from non-compliant material.

* * * * *